(12) United States Patent
Eden et al.

(10) Patent No.: US 8,557,539 B2
(45) Date of Patent: Oct. 15, 2013

(54) OPTICAL METHOD AND DEVICE FOR THE DETECTION AND ENUMERATION OF MICROORGANISMS

(75) Inventors: Gideon Eden, Ann Arbor, MI (US); Ruth Eden, Ann Arbor, MI (US)

(73) Assignee: BioLumix Inc., Ann Arbor, MI (US)

( * ) Notice: Subject to any disclaimer, the term of this patent is extended or adjusted under 35 U.S.C. 154(b) by 1463 days.

(21) Appl. No.: 11/766,223

(22) Filed: Jun. 21, 2007

(65) Prior Publication Data
US 2008/0176273 A1    Jul. 24, 2008

Related U.S. Application Data

(60) Provisional application No. 60/857,917, filed on Nov. 10, 2006.

(51) Int. Cl.
*C12Q 1/08* (2006.01)
*C12N 1/02* (2006.01)
*C12M 1/34* (2006.01)

(52) U.S. Cl.
USPC ............. 435/40; 435/34; 435/261; 435/288.7

(58) Field of Classification Search
USPC ............ 435/30, 32, 34, 261, 287.1, 288.7, 40
See application file for complete search history.

(56) References Cited

U.S. PATENT DOCUMENTS

| | | | |
|---|---|---|---|
| 4,264,728 A * | 4/1981 | Wilkins | 435/5 |
| 4,945,060 A | 7/1990 | Turner et al. | |
| 5,094,955 A | 3/1992 | Calandra et al. | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,366,873 A | 11/1994 | Eden et al. | |
| 5,403,741 A * | 4/1995 | Holbrook | 435/288.2 |
| 6,395,537 B1 | 5/2002 | Eden et al. | |
| 6,855,514 B2 * | 2/2005 | Ogawa | 435/34 |
| 2006/0019331 A1 * | 1/2006 | Eden | 435/34 |

FOREIGN PATENT DOCUMENTS

| | | |
|---|---|---|
| EP | 0523805 A2 | 1/1993 |
| WO | WO 96/14429 | 5/1996 |

\* cited by examiner

*Primary Examiner* — Michael Hobbs
(74) *Attorney, Agent, or Firm* — Young Basile Hanlon & MacFarlance, P.C.; Denise M. Glassmeyer

(57) ABSTRACT

A new device and method for detecting the presence of living microorganisms in test samples are described. The device comprises a container with at least one section transparent to light, a growth zone located in said container containing a mixture of growth media capable of supporting growth of the microorganisms, and at least one indicator substrate that changes its optical properties due to growth of the microorganisms. A detection zone is located in the container adjacent to the transparent section, and a barrier layer comprising porous solid material separates the two zones, allowing diffusion of molecules and ions of metabolic by-products of the organisms, while preventing microorganisms and particulate matter of the test sample from penetrating into the detection zone.

23 Claims, 3 Drawing Sheets

OPTICAL METHOD AND DEVICE FOR THE DETECTION AND ENUMERATION OF MICROORGANISMS

CROSS REFERENCE TO RELATED APPLICATIONS

This patent application claims the benefit of provisional patent application No. 60/857,917 filed Nov. 10, 2006.

BACKGROUND AND PRIOR ART

The presence and enumeration of microorganisms in industrial samples have been traditionally determined by growing the microorganisms on the surface of agar in Petri dishes and counting the colonies. In the last two decades, other tests have been practiced for clinical and industrial specimens. These methods are based on culturing the specimens in liquid media and monitoring the metabolites generated during the growth of the micro-organisms. Several systems, such as the BACTOMETER® (bioMerieux, Hazelwood, Mo., USA), BACTRAC® device (Sy-Lab, Neupurkersdort, Austria), MALTHUS SYSTEMS® device (Lab M, Crawley, UK) and the RABIT® device (Bioscience International, Bethesda, Md., USA), are based on monitoring the electrical properties of the media measured via two metallic electrodes immersed in the growth media. The conductivity and capacitance of the electrode-media combination is measured by applying AC electrical current via the electrodes in the liquid media.

A novel and practical approach of culturing and monitoring microorganisms (bacteria, yeasts and molds) in test samples in the presence of interfering materials has been developed and successfully commercialized utilizing optical indicator substrates. One such product has been demonstrated by Turner, et al. (U.S. Pat. No. 4,945,060), Calandra, et al. (U.S. Pat. No. 5,094,955), Thorpe, et al. (U.S. Pat. No. 5,162,229), Di Guiseppi, et al. (U.S. Pat. No. 5,164,796), and Turner, et al. (U.S. Pat. No. 5,217,876). The basic principle of this device is to affix a disposable sensor to the interior surface of a transparent container that can monitor pH changes in the liquid media or the production of $CO_2$ when the microorganisms grow and metabolize. The sensor comprises a solid composition or membrane with an indicator substrate immobilized on or within it. The sensor is placed flush against the inside surface of a container, such that the indicator substrate is visible from outside, and sealed to prevent the interfering compounds from getting between it and the container surface. In these embodiments the sensor is separated from the specimen and its growth media by a membrane or solid layer that permits the passage of gas molecules but prevents passage of ions. These devices are therefore characterized by two distinctive phases: (a) liquid phase that includes the growth media where the specimen is incubated and (b) solid phase in which the indicator substrate is embedded. In these devices, no growth media is present in the solid phase and no indicator substrate is present in the media. Practically, since sensors are based upon diffusion of $CO_2$ gas (U.S. Pat. No. 5,217,876), they do require that the container is sealed during the incubation time so that the generated gas is pressurized through the sensor and cannot escape the container (U.S. Pat. No. 4,945,060). Consequently, these devices are limited to the determination of presence or absence of microorganisms in the tested samples which is adequate for clinical and sterility tests. Due to the solid nature of the sensor, the diffusion rate of the metabolites to the sensor is quite slow and may not be consistent for duplicate samples and, consequently, is inadequate for enumeration tests. The clear advantage of these devices is that they can be thermally sterilized (e.g., using autoclave at 121° C.) and, consequently, can be used for highly demanding sterility tests.

Another practical approach has been developed by Eden, et al. (U.S. Pat. No. 5,366,873), which is most suitable for food, dairy, and beverage samples. With this approach, the test container contains two distinct phases: (a) liquid phase, which is a mixture of growth media and indicator substrate, and (b) semi liquid phase, comprising a semi-liquid matrix, such as agar, and identical liquid compounds present in the liquid phase. Liquid molecules and ions can quickly diffuse between the two phases which are in equilibrium. The diffusion rate is higher in this device relative to the Turner device (U.S. Pat. No. 4,945,060), and its consistency makes it adequate for enumeration tests. The disadvantage of this device is that the semi-liquid phase disintegrates in higher temperatures and, therefore, the device cannot be thermally sterilized. Consequently, it cannot be used for clinical and sterility tests. Another disadvantage of this device is that the agar occasionally gets dislodged during transportation.

SUMMARY OF THE INVENTION

This invention provides a device and method for optically monitoring growth of microorganisms present in a test sample, using growth media and indicator substrates that change their optical properties when microorganisms grow and metabolize. The device can be used to determine the presence or absence of bacterial contamination, to enumerate the microorganisms, to provide antimicrobial susceptibility determinations, and to carry out preservative challenge tests.

The purpose of the invention is to provide a device that is capable of monitoring the growth of microorganisms utilizing optical principles, based on new physical structure, and which is adequate for presence and absence tests, including sterility, enumeration evaluations, culture activity tests (such as starter culture activity), antimicrobial susceptibility tests, and preservative effectiveness tests (challenge tests). Unlike the Eden, et al. device, above, this new device can be thermally sterilized but also enjoys the faster diffusion characteristics of the Eden device (U.S. Pat. No. 5,366,873).

DESCRIPTION OF THE PREFERRED EMBODIMENT

Figure 1:
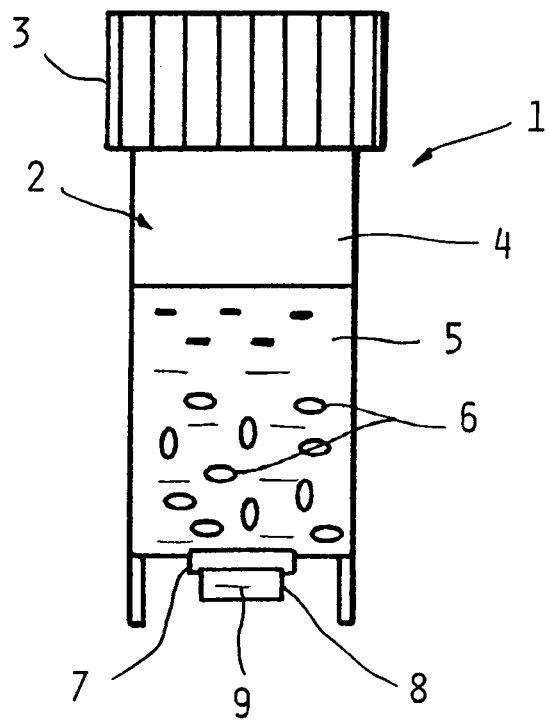
FIG. 1 is a side elevational view of a preferred embodiment of a device according to the invention.

As illustrated in FIG. 1, the device 1 consists of a container 2 used to incubate a test sample in liquid growth media. The container 1 is preferably a plastic vial transparent to light in the visible range and at least a fraction of the long ultraviolet range. For example, polycarbonate can be used which is transparent to the entire visible spectrum and to long ultraviolet radiation above 350 nanometers. The container 2 can be sealed with a cap 3 which can be made of polycarbonate as well. Preferably, both the container 2 and the cap 3 can be thermally sterilized at 121° C., and polycarbonate can indeed endure such temperature.

At the bottom part of the container 2, a rectangular window 8 is embedded. The window 8 has 2 parallel opposing surfaces (one surface is shown in the figure) and should be transparent to light, as indicated above. The internal volume of the container 2 consists of a head space 4, growth zone 5, and detection zone 9. As shown in the figure, a liquid mixture of reagents is poured into the container to occupy both zones 5 and 9. A barrier layer 7 separates between zone 5 and 9, blocking any particulate matter 6 from penetrating into the detection zone 9. The barrier material also prevents microorganisms from penetrating to the detection zone. The barrier layer can be any porous material that can diffuse liquid molecules and ions, with selected pore size designed to block particulate matter consisting of either sample particles or microorganisms present in the growth zone 5. The barrier layer can be a porous membrane, such as PALL SUPOR®, which has an average pore size of 0.1-1.5 micron, or other porous thick material, such as POREX® 4897 sheet. The pore size should be less than 2 micron.

The barrier layer 7 is the heart of the new technology. It provides continuity of the liquid phase in zones 5 and 9, while preventing optically interfering substances from reaching the detection zone 9. This structure enables visual observations and optical readings in the window that are unmasked by any interference resulting from the sample itself or turbidity of microorganisms.

The liquid phase in the container is a mixture of growth media and at least one indicator substrate. The growth media enables efficient growth of microorganisms originating from the test sample. Several specific and non-specific media can be used, such as mPCB (Difco, Becton Dickenson and Company, Sparks, Md., USA) with Bromocresol Purple as an indicator for total aerobic plate count, or CM-Coliform Medium (bioMerieux, Hazelwood, Mo., USA). Selective media for the detection of molds and yeast, or selected groups of organisms, such as *Staphylococcus, E. coli*, or lactic acid bacteria can be used. The indicator substrate is a chemical reagent capable of changing its optical properties in the presence of metabolic by-products generated by the growing microorganisms. Practically, the amount and concentration of the indicator substrate is chosen so that the entire mixture of the media and indicator significantly changes its optical properties as a result of microbial growth. Suitable are several dyes that change their colors due to either pH or oxygen reduction indicator (Redox). Examples of indicators that can be used in the visible light range include pH indicators, such as Bromocresol Purple, Chlorophenol Red, Brothymol blue (Sigma-Aldrich, St. Louis, Mo., USA), and reduction indicators, such as Methylen Blue, Resazurin and Tetrazolium (Sigma-Aldrich, St. Louis, Mo., USA). Fluorescence compounds, with changes of properties in the UV range, can be used as indicator substrates, such as a variety of Umbelliferones and Coumarins. For example, 4-methyl-umbelliferyl-β-D-glucuronide (MUG) (Sigma-Aldrich, St. Louis, Mo., USA), can be used in conjunction with selective media to detect *E. coli*. 4-methyl-umbelliferyl phosphate (MUP) (Sigma-Aldrich, St. Louis, Mo., USA) can be used as many organisms metabolize this compound to create fluorescence. PYR (pyroglutamyl aminopeptdase reaction) is useful in the identification of group A streptococci, and L-pyroglutammyl-7-amino-4-methylcoumarin can be used as an indicator of PYR activity. There are many other chromomeric and enzymatic compounds that can be utilized with the current invention.

The liquid in the growth zone 5 is in molecular equilibrium with the liquid in the detection zone 9. Molecules of the growth media and the indicator substrate can rapidly diffuse back and forth. When the hydrostatic pressure of zones 5 and 9 are equal, no flow of liquid takes place and the only transfer of material is due to a diffusion process that takes place whenever the equilibrium is disturbed. During incubation of the sample in the growth media in the growth zone 5, living organisms grow and metabolize, generating metabolic by-products in the liquid. For example, fermenting microorganisms break glucose molecules into other compounds, including H+ ions that lower the liquid pH. Since the metabolites are initially not present in the detection zone 9, the chemical equilibrium is momentarily disturbed and the metabolites diffuse from the growth zone 5 into the detection zone 9 through the barrier 7. As a result, the indicator substance present in both zones gradually changes its optical properties as more metabolites are generated and diffused. While those changes are difficult to observe or measure in the growth zone 5 due to the sample interference, they are easy to monitor in the detection zone 9 that substantially remains clear during the duration of the test. The principle of this device is therefore totally different than the Turner device described in the prior art, in which the pH indicator substrate is embedded and confined to only the sensor's solid matrix, and the media is present and confined to the liquid (incubation) phase and there is no chemical equilibrium between these phases at any given time.

Figure 2:
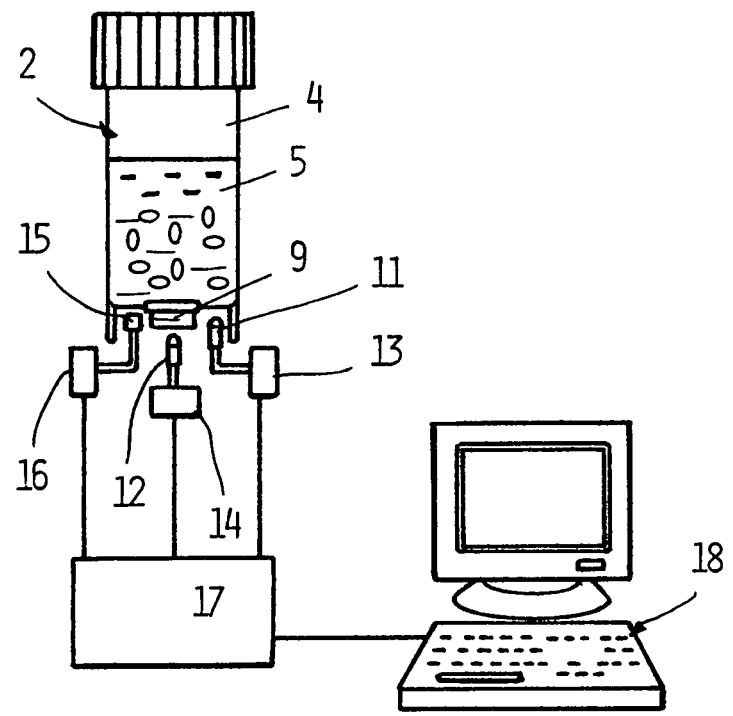
FIG. 2 is a diagram of an experimental setup of an automated reader associated with the device shown in FIG. 1.

An experimental setup is illustrated in FIG. 2 in which the container 2 is combined with optical instrumentation to test the methodology. There are two light source units, a visible light source 11 and an ultraviolet light source 12, which may be incandescent light bulbs, light-emitting diodes, or gas discharge tubes. The visible light source 11 and the ultraviolet source 12 receive their energy and are controlled by controllers 13 and 14, respectively. A single photo-detector 15 is used to detect the energy generated by the interaction of the energy from the light sources with the indicator substrate in the detection zone 9. The photo-detector can either be a photo diode, photo transistor, photon multiplying tube (PMT) or any other light-sensitive device. An amplifier 16 amplifies the analog signal detected by the photo-detector 15. An electronic processor 17 activates the light sources 11 and 12 by sequentially switching on the controllers 13 and 14, and processes the analog signal received by the amplifier 16. A computer 18 receives the processed data, stores it in non-volatile memory, and provides real-time analysis of the stored data.

The tested sample is placed in the container 2 in which the incubation and detection zones 5 and 9 have been pre-filled with the liquid mixture of the growth media and indicator substrates. The container is closed with the cap 3, allowing a sufficient volume of air in its head space 4. The container 2 is placed in a fixture assembly which includes the light sources 11 and 12 and the photo-diode 15. The fixture assembly is placed into an incubator which is set to optimal temperature for growth of the target microorganisms. In preset time intervals (i.e., 10 minutes), the controller 17 sequentially switches on the light sources 11 and 12 for a fraction of a second. The photo-detector 15 detects visible light related data followed by ultraviolet light data. Both signals are amplified by the amplifier 16 and converted to digital data by the processor 17 which also sends them to the computer 18. The data is stored and analyzed during each time interval.

Example 1

Figure 3:
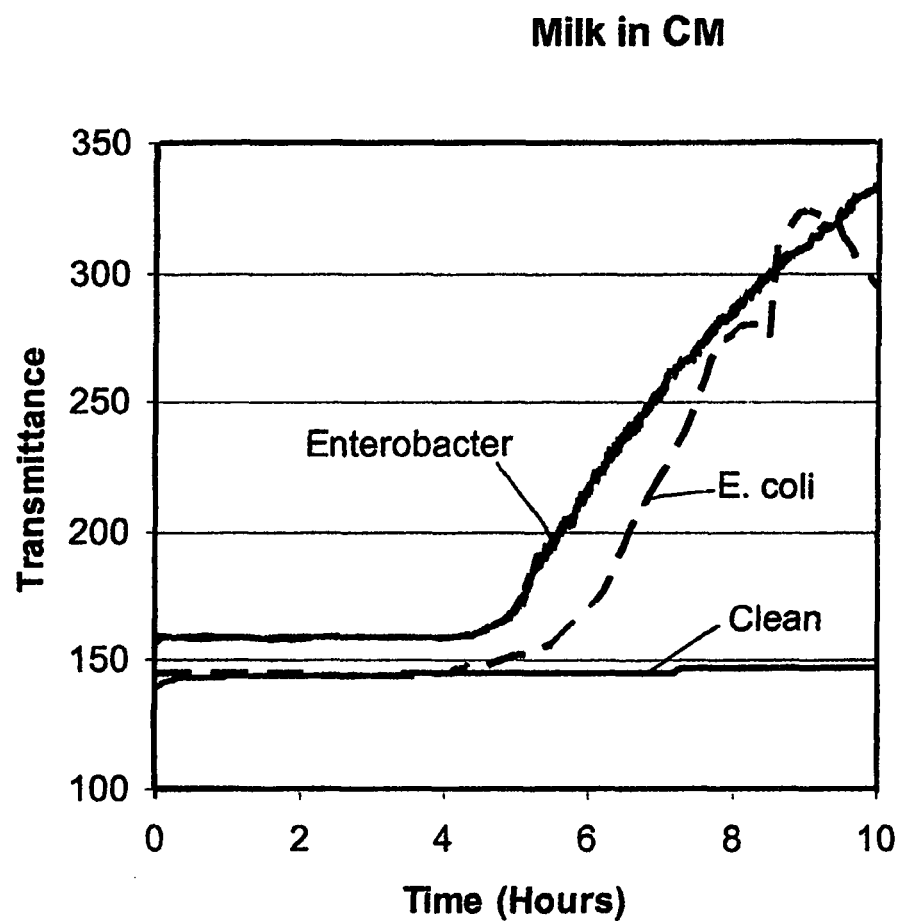
FIG. 3 is a chart of a plot of experimental data of a milk sample.

Three containers were prepared with a barrier layer made of hydrophilic POREX disks (material #4897) and pre-filled with 9 ml of mixture of coliform media (BioMérieux CM) that also contains an adequate amount of Bromocresol Purple. Bromocresol Purple changes its color from purple to yellow due to fermentation of lactose resulting in the reduction of pH. Three samples of 1 ml of pasteurized milk were prepared, one inoculated with *E. coli*, another with *Enterobacter aerogenes*, and the third remained un-inoculated. Each 1 ml sample was pipetted into one of the three containers and placed into the fixture assembly inside an incubator set at 35° C. Data corresponding to the transmittance value picked up by the photodiode 15, due to activation of the light source 11, was collected and stored every 10 minutes. The collected data for each of the three containers is shown in FIG. 3. It is evident that the clean sample did not change the pH in the container during the duration of the test, and, consequently, the recorded pattern is flat. The inoculated samples resulted in significant pH changes that took place after approximately 4.5 hours of incubation. This time interval, defined as Detection Time, in which a rapid change of the indicator substrate takes place, is inversely proportional to the initial concentration of the microorganisms in the test sample, as demonstrated in the mathematical analysis below.

Example 2

Figure 4:
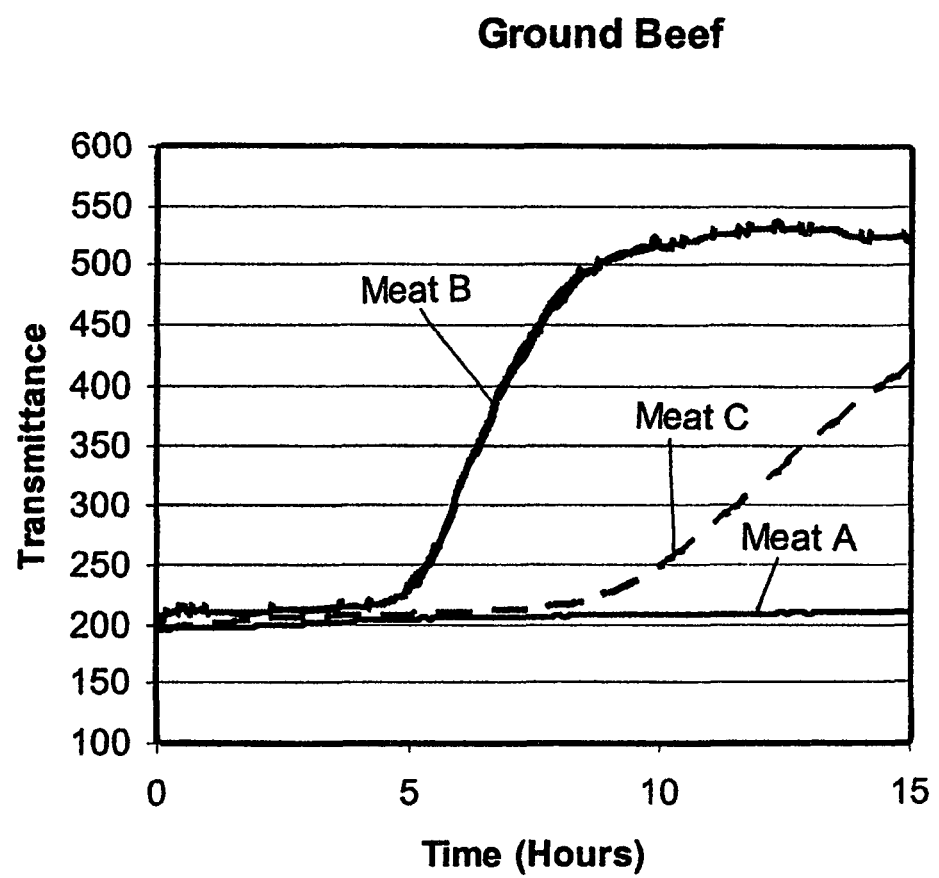
FIG. 4 is a chart of a plot experimental data of a ground meat sample.

Similar tests were carried out with three different samples of ground beef. The growth media is mPCB (Difco, Becton Dickenson and Company, Sparks, Md., USA), which is a non-selective medium for total aerobic count, mixed with 20 mg./liter of Bromocresol Purple. Each container contained 9 ml of mixture of media and indicator. Each of the meat samples was diluted 1:10 in Butterfield's phosphate buffer, 2 ml of each sample was added into each container, and the containers were placed in an incubator and monitored over 15 hours. The meat sample, shown as Meat A in FIG. 4, was fresh and relatively clean from microorganisms. The sample Meat C resulted from letting the same meat of Meat A stay at room temperature for 8 hours, and Meat B stayed at room temperature overnight. As expected, Meat B resulted in short Detection Time of approx. 5 hours, Meat C detected in 9.5 hours, and the "clean" sample did not detect during the hours duration of the test. In addition, it can be seen that the slopes of the curves immediately after their Detection Times were also different. The slope of Meat C is smaller than that of Meat B. The slope, that can be measured as the change in transmittance units during a specific time interval after detection (i.e., 1 hour), follows the logarithmic growth pattern of the microorganisms for the specific application, specific growth media, and the applied incubation temperature.

As mentioned above, the Detection Time and the slope are indicative of the microorganisms' initial concentration in the test sample and their activity. Therefore, the device can also be utilized for antimicrobial susceptibility tests and challenge tests. In antimicrobial susceptibility tests, the influence of antibiotic agents on target microorganisms can be tested by preparing multiple containers with various antimicrobial agents (such as antibiotics) with multiple concentrations added to the media. The patient isolated organisms are inoculated to all the containers in equal numbers. A reference container without any antimicrobial agent is also used. By comparing the delays in the corresponding Detection Time and the reduction of slope, of the containers with the specific antimicrobial agents relative to the reference container, the effectiveness of each agent at a specific concentration can be determined. Another use of the device is to carry out challenge tests used to determine the effectiveness of preservatives on specific products, such as cosmetics and toiletry products. In principal, those tests are similar to the susceptibility tests. The tested product is artificially inoculated by target microorganisms, and various preservatives at multiple concentrations are added. A calibration curve relating numbers of organisms with Detection times is first created. Comparing the resulting Detection Times and slopes of every container to a reference container without any preservative, the effectiveness of each preservative at the specific concentration can be determined, as well as the log reduction in numbers of organisms.

Mathematical Analysis of Detection Times

When a single strain of microorganisms is introduced to liquid growth media and incubated, there exists an initial phase, defined as the lag phase, in which the microorganisms metabolize but do not significantly multiply, resulting in lag time $t_L$.

During the lag phase, the microorganisms' concentration $C_B$ is:

$$C_B(t) = C_{B0} \quad t \leq t_L \tag{1}$$

where $C_{B0}$ (or CFU) is the initial concentration of the microorganisms.

After the lag phase the logarithmic phase initiates when the microorganisms approximately double every generation time $t_g$. At generation number n the number of microorganisms is:

$$C_B(n) = C_{B0} \cdot 2^n$$

Taking into account the delay time $t_L$ and that $n = t/t_g$, it follows that:

$$C_B(t) = C_{B0} \cdot e^{(t-t_L) \cdot \ln 2/t_g} \quad t \geq t_L \tag{2}$$

Assuming that each organism generates $K_B$ ions in the media per unit time, the total number of generated ions $C_S$ is:

$$C_S(t) = K_B \cdot \int_0^t C_B(t) dt \quad t \geq 0$$

wherein $K_B$ is defined as the bacterial activity expressed in 1/minute units.

Although during the lag phase microorganisms do not multiply, they are still metabolizing and generating ions to the solution. From (1) it follows that:

$$C_S(t) = K_B \cdot \int_0^t C_{B0} dt = K_B \cdot C_{B0} \cdot t \quad t \leq t_L$$

During the logarithmic phase, the net ionic concentration is the sum of its value at the end of the lag phase and the concentration of ions generated during the logarithmic phase multiplication. From (1) and (2) it follows that:

$$\begin{aligned} C_S(t) &= K_B \cdot \int_0^{t_L} C_{B0} dt + K_B \cdot \int_{t_L}^t C_{B0} \cdot e^{(t-t_L) \ln 2/t_g} dt \\ &= K_B \cdot C_{B0} \cdot t_L + \frac{K_B \cdot C_{B0} \cdot t_g}{\ln 2} \cdot [e^{(t-t_L) \ln 2/t_g} - 1] \\ &= K_B \cdot C_{B0} \cdot \left(t_L - \frac{t_g}{\ln 2}\right) + \frac{K_B \cdot C_{B0} \cdot t_g}{\ln 2} \cdot e^{(t-t_L) \ln 2/t_g} \end{aligned} \tag{3}$$

The first term in (3) becomes negligible for $t \gg t_L$. Consequently, the total ionic increase in time is:

$$C_S(t) = \frac{K_B \cdot C_{B0} \cdot t_g}{\ln 2} \cdot e^{(t-t_L)\ln 2/t_g}$$

At some instant, defined as Detection Time $t_D$, the ionic concentration $C_S$ exceeds the initial ionic concentration $C_{SI}$ and measurable color change takes place. At that instance:

$$C_{SI} = C_S(t) = \frac{K_B \cdot C_{B0} \cdot t_g}{\ln 2} \cdot e^{(t_D-t_L)\ln 2/t_g}$$

and $$t_D = t_L + \frac{t_g}{\ln 2} \cdot \ln \frac{C_{SI} \cdot \ln 2}{K_B \cdot K_{B0} \cdot t_g} \quad (4)$$

Rearranging the term of (4) and defining $C_{B0}$ as the number of colony forming units CFU we get:

$$CFU = \log^{-1}\left(\log\frac{C_{si} \cdot \ln 2}{K_B \cdot t_g} - \frac{\log 2}{t_g} \cdot (t_D - t_L)\right) \quad (5)$$

and by combining the intrinsic parameters to empirical coefficients A and B we get:

$$\log(CFU) = A - B \cdot t_D \quad (6)$$

Equation 6 provides a calibration tool by correlating experimental detection times of multiple samples to their Colony Forming Units as measured by standard plating technique. Applying linear regression analysis (best fit line) to the experimental data, the coefficients A and B can be easily determined.

The invention claimed is:

1. An apparatus for detecting the presence of microorganisms in a test sample comprising:
    optical instrumentation including a light source unit and a photodetector;
    a container with at least one section transparent to light;
    a growth zone configured to receive the test sample, the growth zone located in the container, containing a mixture of liquid growth media capable of supporting growth of the microorganisms, at least one dye indicator dispersed in the growth media, the dye indicator composed of material that chemically interacts with metabolic products of growing microorganisms to effect color change of the dye indicator;
    a detection zone, the detection zone configured to detect the presence of growing microorganisms, the detection zone located in a container adjacent to the transparent section and containing an identical mixture of the liquid growth media and the dye indicator substrate;
    a hydrophilic membrane interposed between said growth and detection zones, the membrane configured to allow diffusion of molecules of the liquid growth media, the dye indicator, and molecules of the metabolic products of growing microorganisms, back and forth between the growth and the detection zones, wherein the membrane is configured to prevent microorganisms and particulate matter of the test sample from penetrating into the detection zone; and
    wherein said light source produces light that passes through said detection zone prior to being detected by said photodetector and wherein changes in the color of the dye indicator in the detection zone indicate presence of microorganisms growing in the growth zone.

2. The device of claim 1 wherein the maximal pore size of said membrane is less than 1 micrometer.

3. The device of claim 1 wherein said hydrophilic membrane comprises a polymer.

4. The device of claim 1 wherein said dye indicator is a dye capable of changing its visible wavelength due to the metabolic products of growing microorganisms.

5. The device of claim 1 wherein said color indicator substrate is fluorescence a dye capable of changing its fluorescence properties due to the metabolic products processes of the growing microorganisms.

6. A method for detecting the presence of living microorganisms in a test sample, comprising the steps of:
    introducing the test sample into the growth zone of the device of claim 1;
    incubating the microorganisms in the growth media and allowing metabolic processes to generate by-products into the mixture of the media and the indicator substrate present in the growth zone, thereby changing the optical properties of the indicator substrate;
    allowing the by-products to diffuse into the detection zone through the hydrophilic membrane that blocks the microorganisms and the particulate matter of the test sample from reaching the detection zone; and
    observing the change in the optical properties of the indicator substrate in the detection zone through the transparent section.

7. The method of claim 6 further including the steps of:
    aiming an electromagnetic energy source at the transparent section; and
    detecting the reactive electromagnetic energy resulting from the interaction of the electromagnetic energy with the indicator substrate present in the detection zone.

8. The method of claim 7 wherein said electromagnetic energy source is a visible light source and the indicator substrate is a visible dye.

9. The method of claim 8 wherein said electromagnetic energy source is a light-emitting diode.

10. The method of claim 7 wherein said electromagnetic energy source is an ultraviolet light source and the indicator substrate is a fluorescence dye generating visible reactive energy.

11. The method of claim 10 wherein said electromagnetic energy source is an ultraviolet light-emitting diode.

12. The method of claim 10 wherein said electromagnetic energy source is an ultraviolet gas discharge tube.

13. The method of claim 7 wherein a photo detector is utilized for the detection of the reactive electromagnetic energy.

14. The method of claim 13 wherein the photo detector is a photo diode.

15. The method of claim 13 wherein the photo detector is a photo transistor.

16. The method of claim 13 wherein the photo detector is a photon multiplying tube (PMT).

17. The method of claim 7 wherein said electromagnetic energy source comprises a multiple color light-emitting diode.

18. The method of claim 17 wherein said electromagnetic energy source further comprises an ultraviolet light-emitting diode.

19. The method of claim 17 wherein said electromagnetic energy source further comprises an ultraviolet gas discharge tube.

20. A method of enumerating living microorganisms in a test sample, comprising the steps of:
  applying the steps described in claim 7 and recording the detected reactive electromagnetic energy at predetermined time intervals as time sequence data;
  analyzing the sequence data to determine the Detection Time, in which the difference between a predetermined number of consecutive data points in the sequence data changes to follow the growth pattern of the living microorganisms; and
  evaluating the number of the living microorganisms in the samples by applying the equation:

$$CFU = \log^{-1}\left(\log\frac{C_{si}\ln2}{K_B t_g} - \frac{\log 2}{t_g}(t_D - t_L)\right)$$

wherein:
  CFU is the colony forming units;
  log denotes the 10 base logarithmic function;
  ln denotes the natural logarithmic function;
  $C_{si}$ is the initial concentration of the dye substrate modifying reagents;
  $K_B$ is the bacterial activity;
  $t_g$ is the bacterial generation time;
  $t_D$ is said Detection Time; and
  $t_L$ is the time duration of the lag phase.

21. The method of claim 20 wherein the coefficients of said equation are determined empirically by performing a statistical best-fit linear regression analysis to derive from experimental data values A and B of the equation:

$$\text{Log}(CFU) = A - B \cdot t_D$$

wherein said experimental data consists of a multiplicity of tests for different test samples, each consisting of finding the CFU value using traditional plate counts methodology and the corresponding Detection Time $t_D$.

22. A method for testing the susceptibility of microorganisms to antimicrobial agents, comprising the steps of:
  dividing a sample of the microorganisms to a test sample and a reference sample with identical volumes and concentrations;
  mixing the test sample with a target antimicrobial agent at a specific concentration to form a susceptibility test sample;
  applying the steps described in claim 7 to the susceptibility test sample and recording the detected reactive electromagnetic energy at predetermined time intervals as a sample time sequence data;
  analyzing said sample sequence data to determine the sample Detection Time in which the slope calculated amongst a predetermined number of consecutive data points in said sample sequence data changes to follow the intrinsic slope of the logarithmic growth pattern of the microorganisms;
  applying the steps described in claim 7 to the reference sample and recording the detected reactive electromagnetic energy at predetermined time intervals as a reference time sequence data;
  analyzing said sample sequence data to determine the reference Detection Time in which the slope calculated amongst a predetermined number of consecutive data points in said reference time sequence data changes to follow the intrinsic slope of the logarithmic growth pattern of the microorganisms; and
  comparing the sample Detection Time to the reference Detection Time and providing criteria to determine the susceptibility of the microorganisms based upon said comparison.

23. A method for testing the effectiveness of a preservative agent to reduce the growth of microorganisms in a sample, comprising the steps of:
  dividing a sample to a test sample and a reference sample with identical volumes and concentrations;
  mixing the test sample with the preservative agent at a specific concentration ratio to form a challenge test sample;
  applying the steps described in claim 7 to the challenge test sample and recording the detected reactive electromagnetic energy at predetermined time intervals as a sample time sequence data;
  analyzing said sample sequence data to determine the sample Detection Time in which the slope calculated amongst a predetermined number of consecutive data points in said sample time sequence data changes to follow the intrinsic slope of the logarithmic growth pattern of the microorganisms;
  applying the steps described in claim 7 to the reference sample and recording the detected reactive electromagnetic energy at predetermined time intervals as a reference time sequence data;
  analyzing said sample sequence data to determine the reference Detection Time in which the slope calculated amongst a predetermined number of consecutive data points in said reference time sequence data changes to follow the intrinsic slope of the logarithmic growth pattern of the microorganisms; and
  comparing the sample Detection Time to the reference Detection Time, and providing criteria to determine the effectiveness of the preservative based upon said comparison.

* * * * *